United States Patent
Chung et al.

(10) Patent No.: US 10,058,712 B2
(45) Date of Patent: Aug. 28, 2018

(54) SOMATIC SENSATION INDUCTION SYSTEM USING PULSE LASER AND MEDIUM OF HIGH ABSORPTION COEFFICIENT

(71) Applicants: Konkuk University Glocal Industry-Academic Collaboration Foundation, Chungcheongbuk-do (KR); Industry-Academic Cooperation Foundation, Chosun University, Gwangju (KR)

(72) Inventors: Soon-Cheol Chung, Chungju-si (KR); Jae-Hoon Jun, Seoul (KR); Jong-Rak Park, Gwangju (KR); Seungmoon Choi, Pohang-si (KR); Hyung-Sik Kim, Chungju-si (KR); Ji-Sun Kim, Chungju-si (KR)

(73) Assignees: KONKUK UNIVERSITY GLOCAL INDUSTRY-ACADEMIC COLLABORATION FOUNDATION, Chungju-si, Chungcheongbuk-Do (KR); INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 447 days.

(21) Appl. No.: 14/856,905

(22) Filed: Sep. 17, 2015

(65) Prior Publication Data
US 2016/0367835 A1    Dec. 22, 2016

(30) Foreign Application Priority Data
Jun. 22, 2015    (KR) .................... 10-2015-0088458

(51) Int. Cl.
*A61N 5/06* (2006.01)
*A61N 5/067* (2006.01)

(52) U.S. Cl.
CPC ......... *A61N 5/0622* (2013.01); *A61N 5/0616* (2013.01); *A61N 2005/067* (2013.01);
(Continued)

(58) Field of Classification Search
CPC ............... A61N 5/0622; A61N 5/0616; A61N 2005/0659; A61N 2005/0663; A61N 2005/067
See application file for complete search history.

(56) References Cited

U.S. PATENT DOCUMENTS

| | | | | |
|---|---|---|---|---|
| 6,162,211 A | * | 12/2000 | Tankovich | ........... A61B 18/203 606/9 |
| 6,974,451 B2 | * | 12/2005 | Altshuler | ............. A61B 18/203 606/13 |

(Continued)

FOREIGN PATENT DOCUMENTS

| | | |
|---|---|---|
| JP | 2015-006443 A | 1/2015 |
| KR | 10-2013-0110235 A | 10/2013 |

(Continued)

OTHER PUBLICATIONS

Hojin Lee et al., "Mid-Air Tactile Stimulation Using Laser-Induced Thermoelastic Effects: The First Study for Indirect Radiation", World Haptics Conference, Jun. 2015, Chicago.

*Primary Examiner* — Quang D Thanh
(74) *Attorney, Agent, or Firm* — LRK Patent Law Firm

(57) ABSTRACT

The present invention relates to a system for fundamentally eliminating skin damage caused by direct radiation of a laser beam on the skin of a user and inducing a somatic sensation on the skin within a safety standard by radiating a pulse laser beam on a medium attached to the skin of the user on which the somatic sensation is desired to be induced. Particularly, (Continued)

the present invention relates to a somatic sensation induction system which can induce a somatic sensation of various feelings delivered to a user by adjusting an absorption coefficient of a medium contacting with the skin of a user, energy intensity and a repetition rate of a radiated laser beam and the like.

6 Claims, 4 Drawing Sheets

(52) U.S. Cl.
CPC ............... *A61N 2005/0659* (2013.01); *A61N 2005/0663* (2013.01)

(56) References Cited

U.S. PATENT DOCUMENTS

| | | | | |
|---|---|---|---|---|
| 2005/0177208 A1* | 8/2005 | Irwin | ................... | A61N 5/0603 607/94 |
| 2009/0233987 A1* | 9/2009 | Obara | ...................... | A01N 1/02 514/44 R |
| 2014/0046246 A1* | 2/2014 | Ferreira De Sa | .. | A61K 41/0047 604/22 |
| 2015/0133848 A1* | 5/2015 | Bratchenia | ............. | A61B 18/26 604/20 |

FOREIGN PATENT DOCUMENTS

| KR | 10-1340361 B1 | 12/2013 |
|---|---|---|
| KR | 10-2014-0025464 A | 3/2014 |

\* cited by examiner

Red-Red    Red-White

FIG.5

| Beam diameter : 5mm / Episode time : 5s / Layer : Red-White ||||||
|---|---|---|---|---|---|
| | single shot | 5Hz | 20Hz | 35Hz | 50Hz | 60Hz |
| 8.5 mJ | Feeling of touch 85% | Feeling of touch 90% | Feeling of touch 60% / Sensation of vibration 40% | Sensation of vibration 90% | Sensation of vibration 90% | Sensation of vibration 95% |
| 14.1 mJ | Feeling of touch 100% | Feeling of touch 100% | Feeling of touch 70% / Sensation of vibration 30% | Sensation of vibration 90% | Sensation of vibration 100% | Sensation of vibration 100% |
| 21.1 mJ | Feeling of touch 100% | Feeling of touch 100% | Feeling of touch 70% / Sensation of vibration 30% | Sensation of vibration 85% | Sensation of vibration 95% | Sensation of vibration 100% |
| 27.4 mJ | Feeling of touch 100% | Feeling of touch 100% | Feeling of touch 70% / Sensation of vibration 35% | Sensation of vibration 85% | Sensation of vibration 100% | Sensation of vibration 100% |

Legend:
- No feeling
- Diffusive feeling
- Feeling of touch
- Electrical feeling
- Sensation of vibration
- Sensation of vibration + Sensation of heat

SOMATIC SENSATION INDUCTION SYSTEM USING PULSE LASER AND MEDIUM OF HIGH ABSORPTION COEFFICIENT

BACKGROUND OF THE INVENTION

1. Field of the Invention

The present invention relates to a somatic sensation induction system and, more specifically, to a system for fundamentally eliminating skin damage caused by direct radiation of a laser beam on the skin of a user and inducing a somatic sensation on the skin within a safety standard by radiating a pulse laser beam on a medium attached to the skin of the user on which the somatic sensation is desired to be induced.

Particularly, the present invention relates to a somatic sensation induction system which can induce a somatic sensation of various feelings delivered to a user by adjusting an absorption coefficient of a medium contacting with the skin of a user, energy intensity and a repetition rate of a radiated laser beam and the like.

2. Background of the Related Art

A laser device is an apparatus for emitting light using light amplification by stimulated emission of radiation.

Such a laser device emits artificial light of uniform direction, phase and wavelength, and the laser device is much utilized in various industrial fields such as communication, medicine, nano-technology, precision machine tool area and the like since it can control the attributes described above.

Meanwhile, a laser device may be largely implemented in two types of electric generation, i.e., electric generation accompanied by damage to a medium and electric generation unaccompanied by damage to a medium.

The electric generation accompanied by damage to a medium appears due to a laser induced optical breakdown or laser ablation, and such electric generation is utilized in the field of biostimulation, medical operation and the like.

Contrarily, the electric generation unaccompanied by damage to a medium is called as a laser induced thermoelastic effect, referring to electric generation generating a stress wave without damage to a medium, and the laser induced thermo-elastic effect can be utilized for non-destructive inspection, medical imaging and the like.

Recently, studies on laser devices which do not generate biological damage like this is progressed actively, and, particularly, studies for finding a range of attributes of a laser device which does not generate the biological damage are progressed specifically.

However, although a laser device which does not generate damage to a medium, particularly, a biological tissue, as described above is recognized as a meaningful achievement in that skin damage does not occur when a laser beam is radiated on a skin tissue of a human being, there is also a problem in that a stimulus of a sufficient level is not induced on the skin tissue.

The present invention has been made to solve a problem such that a laser device which does not generate damage to a biological tissue like this does not induce a stimulus of a proper magnitude on the biological tissue, and an object of the present invention to provide additional technical elements which can satisfy the technical requirements described above and cannot be easily invented by those skilled in the art.

SUMMARY OF THE INVENTION

Therefore, the present invention has been made in view of the above problems, and it is an object of the present invention to implement electric generation which does not damage a medium when a laser beam is radiated, i.e., electric generation unaccompanied by damage to the skin of a user.

Particularly, another object of the present invention is to provide a somatic sensation induction system for generating a stimulus on a biological tissue contacting with a special medium capable of absorbing light by patching the medium on the biological tissue and radiating a laser beam on the medium.

In addition, another object of the present invention is to provide a system capable of inducing a somatic sensation within a range not damaging the skin of a user by adjusting an absorption coefficient of the medium and various attributes of a radiated laser beam.

The technical problems to be accomplished by the present invention are not limited to the technical problems mentioned above, and unmentioned other technical problems may be included within a range apparent to those skilled in the art from the following descriptions.

The present invention provides a somatic sensation induction system as a means for solving the problems described above. However, the categories of the present invention are not limited by the words themselves and can be interpreted to be diversely extended within the scope including the technical spirits which will be described below.

A somatic sensation induction system according to the present invention includes: a laser radiation device for controlling parameters of a laser beam and radiating the laser beam on one side of a medium; and the medium, one side of which is radiated with the laser beam, and the other side of which contacts with a skin tissue of a user.

In addition, in the somatic sensation induction system, the parameters of the laser beam include energy intensity, pulse width, pulse frequency, stimulation time and beam diameter.

In addition, in the somatic sensation induction system, the medium includes a first layer and a second layer, and the first layer and the second layer respectively have a different color and absorb light of a different wavelength.

At this point, the first layer or the second layer is in red color or white color.

In addition, at this point, the wavelength of the laser beam is any one of 445 nm, 480 nm, 532 nm, 650 nm, 809 nm, 850 nm and 1064 nm.

In addition, at this point, the first layer and the second layer are respectively in red color and white color, and a sensation of touch is induced on the skin tissue of the user by controlling the pulse frequency of the laser beam between 1 Hz and 25 Hz.

On the other hand, the first layer and the second layer are respectively in red color and white color, and a sensation of vibration is induced on the skin tissue of the user by controlling the pulse frequency of the laser beam to be 25 Hz or higher.

BRIEF DESCRIPTION OF THE DRAWINGS

FIG. 5 is a view showing an example of experiment inducing a somatic sensation on a subject by utilizing a somatic sensation induction system according to the present invention, particularly, an example experimented while controlling magnitude of energy and frequency of a pulse.

DETAILED DESCRIPTION OF THE PREFERRED EMBODIMENT

Details of the objects and technical configuration of the present invention and operational effects according thereto will be more clearly understood by the detailed description described below based on the accompanying drawings attached in the specification of the present invention. The embodiments according to the present invention will be hereafter described in detail, with reference to the accompanying drawings.

The embodiments disclosed in this specification should not be interpreted or used to limit the scope of the present invention. It is natural that the description including the embodiments of this specification has various applications to those skilled in the art. Accordingly, certain embodiments disclosed in the detailed description of the present invention are for illustrative purposes to further clearly describe the present invention and are not intended to limit the scope of the present invention to the embodiments.

The function blocks shown in the figures and described below are merely examples of possible implementations. Accordingly, other components may be used in other implementations of the present invention without departing from the spirit and scope of the present invention. In addition, although one or more of the function blocks of the present invention are expressed an individual blocks, one or more of the function blocks of the present invention may be a combination of various hardware and software components executing the same function.

In addition, the expression of 'including' an element is an expression of an 'open type' which merely refers to existence of a corresponding component, and it should not be construed as precluding additional components.

It will be understood that when a constitutional component is referred to as being "connected" or "coupled" to another element, it may be directly connected or coupled to the other element or intervening elements may be present.

Figure 1:
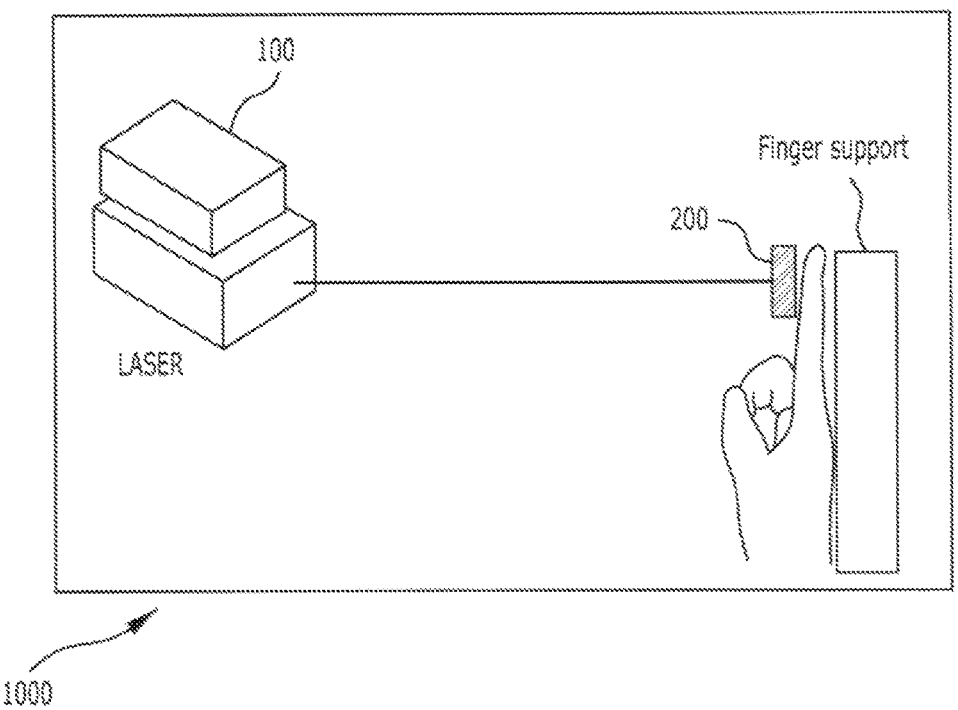
FIG. 1 is a view schematically showing the configuration of a somatic sensation induction system according to the present invention.

FIG. 1 is a view schematically showing the configuration of a somatic sensation induction system 1000 according to the present invention.

According to FIG. 1, a somatic sensation induction system 1000 includes a laser radiation device 100 and a medium 200.

First, the laser radiation device 100 controls various parameters of a laser beam and performs a function of radiating the laser beam to a specific target, specifically, to the medium 200 contacting with a skin tissue of a user, while the parameters are in a controlled state.

In detail, the laser radiation device 100 may include a variety of sub-configurations to perform such a function, and this will be described below in the description of FIG. 4.

The laser radiation device 100 may control parameters such as a pulse width, a pulse frequency, an energy intensity, a laser radiation time and a beam diameter.

In addition, the wavelength of a laser beam mentioned in this detailed description is assumed to be any one of 445 nm, 480 nm, 532 nm, 650 nm, 809 nm, 850 nm and 1064 nm generally used in an industrial field. However, it should be understood that the wavelength of a laser beam in the present invention is not limited to the specific numerical values described above, but the numerical values of the wavelength of a laser beam can be changed within a scope capable of easily implementing the present invention by those skilled in the art.

Meanwhile, the medium 200 is a target to which the laser beam is radiated, and it is characterized in that one side of the medium 200 receives the radiated laser beam, and the other side, i.e., a side opposite to the one side, contacts with a skin tissue of the user.

The medium 200 used in the present invention is a material having an adhesive feature, and, preferably, it may be manufactured using an acrylic foam. At this point, the medium 200 is an adhesive and may be a semi-fluid, i.e., an elastic material, which cannot be clearly distinguished as a solid or a liquid, and the medium 200 is a fully synthetic polymer having attributes of a sleek surface, a colorless color and an excellent adhesiveness. Furthermore, the medium 200 even has properties of excellent heat tolerance, moisture proof and cold tolerance.

The somatic sensation induction system 1000 according to the present invention is distinguished from those of the prior art in that a new configuration of the medium 200 is placed between a skin tissue of a user and the laser radiation device 100 as described above.

That is, in the case of a conventional laser for minimizing biostimulation, although damage does not occur even when a laser beam is directly radiated on a biological tissue of a human being, the stimulus induced on the biological tissue is not sufficiently strong, and the present invention presents a medium 200 capable of absorbing the laser beam as a solution to solve the problem.

If a laser beam is radiated on a biological tissue through the medium 200 as shown in the present invention, it is effective in that i) thermal and thermo-elastic effects can be induced without difference among people since it is less affected by the features of biological tissues different from person to person, ii) a sensation of touch can be induced further safely since the damage caused by direct radiation of a laser beam on the skin can be fundamentally eliminated compared with radiating the laser beam directly on the biological tissue, iii) a further diverse combination of the radiating laser and the medium 200, which is an intervening medium, can be implemented by placing a new constitutional element such as a medium, and, accordingly, the type of induced sensation of touch can be diversified, and iv) diverse thermal and thermo-elastic effects can be induced by controlling a type of medium, thickness of an attachable medium or the like under the same laser condition.

Meanwhile, a method of inducing a sensation of touch on the skin of a user by the somatic sensation induction system 1000 according to the present invention is as follows.

If a laser beam enters the medium 200, optical energy distribution in the medium 200 is changed by optical coefficients (absorption coefficient, scattering coefficient, refractive index and anisotropy factor), and the energy absorbed in the medium 200 induces a thermo-elastic effect and generates a stress wave. Apparently, at this point, all the energy is provided using the absorbed laser beam as a source.

Meanwhile, when a laser beam having a very short pulse width is absorbed in a medium 200, the absorbing portion is locally heated in a moment due to absorption of the laser beam, and the thermo-elastic effect is an effect of transferring energy to the neighboring medium 200 as pressure is locally increased and, at the same time, a pressure wave is generated when the heated portion is thermally expanded in a moment. At this point, the pressure wave transferred to the neighborhood is referred to as a stress wave, and such a stress wave is transferred inside the medium 200 having elasticity in the method described above.

Meanwhile, since the medium 200 contacts with a skin tissue of a user, mechanical deformation of the medium 200 revealed in the series of process described above, such as local expansion, pressure increase or the like, makes the skin tissue of a user feel a sensation of touch.

On the other hand, since the medium 200 is manufactured using a material of good elasticity, it can be applied to various body tissues and external parts of a user, and it has an effect of inducing a sensation of touch on the body tissues having a different shape, such as a finger, a palm, an arm, a leg and the like.

Figure 2:
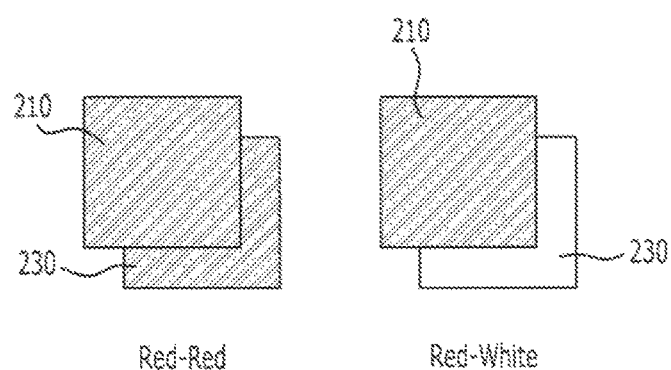
FIGS. 2 and 3 are views showing the detailed configuration of a medium, i.e., the configuration and stacked view of a first layer and a second layer.

Meanwhile, magnitude of the stress wave generated and propagated inside the medium 200 by the absorption of a laser beam is determined according to the mathematical figure shown below.

$$p = \frac{1}{2} p_{max} * \exp[-\mu_a(z - c_s t)]$$ [Mathematical Figure 1]

$$p_{max} = \mu_a \Gamma H_0$$ [Mathematical Figure 2]

At this point, $p_{max}$ denotes the maximum magnitude of the incident stress wave, ca denotes speed of a sound wave, $\mu_a$ denotes absorption coefficient of the medium, $\Gamma$ denotes a Grüneisen constant, $H_0$ denotes absorbed energy density (absorbed fluence).

According to the mathematical FIGS. 1 and 2, the maximum magnitude of the stress wave should be increased in order to induce a further larger sensation of touch to the body tissue. It is understood that a medium of high absorption coefficient and Grüneisen constant is preferably used to this end.

Meanwhile, at this point, the Grüneisen constant is a specific constant of a medium crystal, and it is an index indicating a degree of change of phonon energy (a quasi-particle indicating quantized vibration of a crystal lattice) caused according to thermal expansion.

Figure 3:
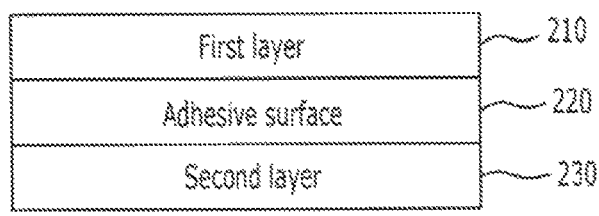

On the other hand, observing from the aspect of acoustic impedance of a medium, a transmission coefficient at the boundary surface of the medium is generally determined as shown in the mathematical FIG. 3.

$$\text{Transmission coefficient } (T) = \frac{p_t}{p_i} = \frac{2Z_2}{Z_2 + Z_1}$$ [Mathematical Figure 3]

At this point, $p_t$ denotes magnitude of a stress wave passing through the medium, $p_i$ denotes magnitude of a stress wave entering the medium, $Z_1$ denotes acoustic impedance of a first medium which is a medium of an incident direction, and $Z_2$ denotes acoustic impedance of a second medium which is a medium of an direction from which the stress wave comes out. At this point, the acoustic impedance is a value calculated, when a specific wave propagates, by dividing pressure on a surface parallel to the wave surface of the specific wave by the volume velocity of the wave passing through the surface. From another viewpoint, the acoustic impedance is resistance that a wave encounters when the wave passes through the medium.

Meanwhile, according to the mathematical FIG. 3, the acoustic impedance of the second medium is preferably larger than the acoustic impedance of the first medium to pass the stress wave through the medium further easily. That is, when two media contact with each other, the transmission coefficient T is increased when the acoustic impedance Z1 of the first medium into which the wave enters is small and the acoustic impedance Z2 of the second medium Z1 from which the wave comes out is large.

That is, if this is applied to the present invention, the medium 200 preferably has an acoustic impedance of a magnitude smaller than that of an acoustic impedance of a body tissue (skin).

Meanwhile, the medium 200 utilized in the present invention may be configured as a stacked structure as shown in FIGS. 2 and 3.

According to FIG. 2, the medium 200 of the present invention is configured of two layers, and, at this point, each of the layers may adjust the absorption coefficient of a corresponding medium 200 by changing color of the layer when the layer is fabricated. Hereinafter, a portion directly absorbing a laser beam is referred to as a first laser 210, and a portion contacting with a skin tissue of a user is referred to as a second laser 230.

As a method of controlling the absorption coefficient of the medium 200, there is a method of changing color of a layer as described above. As is also shown in FIG. 2, when the first layer 210 and the second layer 230 are configured as a red-red medium 200 or a red-white medium 200, the medium 200 has a different absorption coefficient in each case.

At this point, the absorption coefficient is a coefficient indicating a degree of absorbing light by the medium 200, and since the absorption coefficient is generally used for monochromatic light, its value varies according to the wavelength of the light.

Considering definitions of the absorption coefficient described above, the wavelength of an absorbed laser beam and a degree of how easily the wavelength is absorbed can be adjusted in the medium 200 of the present invention depending on selection of a color for each layer.

For example, if the first layer 210 is red, a medium 200 of the red color functions to increase the absorption coefficient for the green color (a wavelength range of 575 nm to 492 nm in the visible light), which is the complementary color of the red color. On the other hand, if the second layer 230 is white, the medium 200 of the white color generally functions to lower the absorption coefficient for all wavelength range. Accordingly, when both the first layer 210 and the second layer 230 are configured in red color, the absorption coefficient for the wavelength of green series is further higher compared with that of a medium 200 configured in red-white color.

On the other hand, according to the present invention, it should be understood that when a laser beam is radiated to the medium 200, a sensation of touch delivered to the user may vary depending on the material used for the medium 200.

That is, a sensation of touch, a sensation of vibration, a sensation of heat and the like can be delivered to a contacting skin tissue of a user by using a medium 200 of an aluminum material, a medium 200 of blue color or the like applying an adhesive using a man-made textile as a base material, other than the medium 200 of acrylic foam of red color mentioned above. Like this, the fact that a sensation felt by a user may vary according to a material used for a medium 200 means that further more kinds of sensations can be provided to a user by the unique features of each medium 200 and various combinations of laser parameters.

For example, under the condition that the diameter of a radiated laser beam, the magnitude of energy and the frequency are the same, a user may feel a mechanical sensation of touch in the case of a medium of acrylic foam, a mechanical sensation of touch and a sensation of heat in the case of a medium fabricated by applying an adhesive on a man-made textile, and only a mechanical sensation of touch of a very weak strength in the case of an aluminum material.

Meanwhile, FIG. 3 is a side view showing the layered structure of the medium 200 of the present invention.

According to FIG. 3, it is understood that the medium 200 stacks planes of a first layer 210 and a second layer 230 and further includes an adhesive surface 220 between the first layer 210 and the second layer 230.

The medium 200 utilized in the present invention is described above with reference to FIGS. 2 and 3.

Hereinafter, the laser radiation device 100, one of the configurations of the present invention, will be described in detail with reference to FIG. 4.

Figure 4:
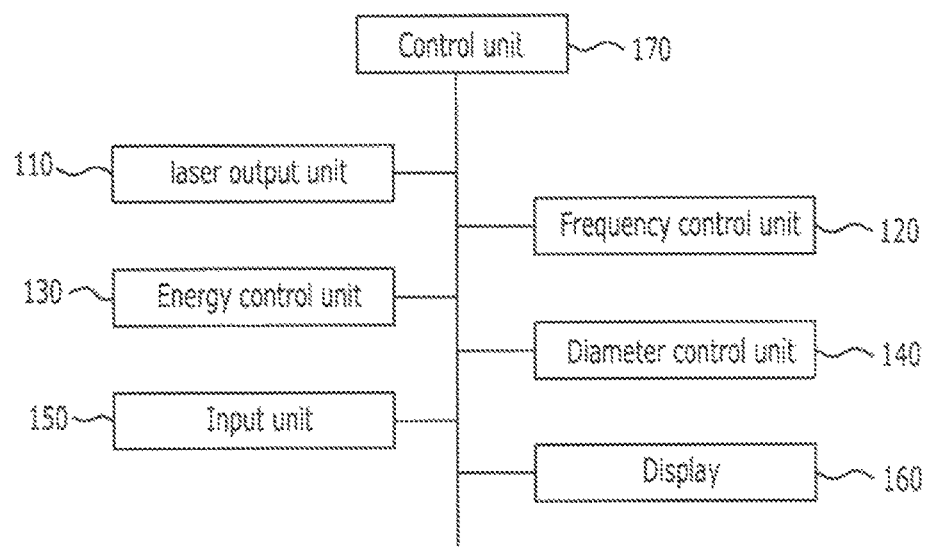
FIG. 4 is a block diagram showing the detailed configuration of a laser radiation device.

According to FIG. 4, the laser radiation device 100 includes a laser output unit 110, a frequency control unit 120, an energy control unit 130, a diameter control unit 140, an input unit 150, a display 160 and a control unit 170. At this point, the control unit 170 and the laser output unit 110 are necessarily included to implement the laser radiation device 100, and other functional unit may be included or excluded according to the need of a user.

First, the laser output unit 110 may include a laser driver and a cooling apparatus as a configuration for outputting a pulse laser beam. The laser driver may include sub-devices such as a laser medium 200, an optical pumping unit, an optical resonator and the like and creates an optical signal for implementing a pulse laser beam. In addition, the cooling apparatus is a device for cooling down the heat which can be generated in the process of creating the optical signal by the laser driver, and it performs a function of preventing malfunctions caused by overheat of the laser driver.

In addition, the laser output unit 110 may be implemented in a variety of methods to generate a pulse laser beam. For example, it may be implemented in a method such as a ruby laser, a neodymium; YAG laser, a neodymium; glass laser, a laser diode, an excimer laser, a dye laser or the like. For reference, the pulse laser beam is generated using a neodymium; YAG laser in the experimental example described below.

Next, the frequency control unit 120 performs a function of controlling pulse frequency per hour of a radiated laser beam. If it is assumed that one cycle is defined as progressing one high state and one low state of a laser output, the frequency control unit 120 may set the number of pulse cycles included in a unit time, e.g., one second, and a user may control the frequency of a pulse laser beam through the setting process.

Meanwhile, it should be understood that the frequency of a pulse laser beam in the present invention can be freely controlled, preferably between 1 Hz and 70 Hz, and, furthermore, it should be understood that a case of 0 Hz frequency, i.e., a single shot of an only one-time laser output without repetition of cycle, can also be set.

Next, the energy control unit 130 performs a function of controlling energy intensity of a radiated laser beam. The energy intensity is expressed by the unit of mill joule (mJ), and the energy intensity in the present invention can be controlled preferably between 0 mJ and 30 mJ.

On the other hand, the energy control unit 130 can be actually implemented by an optical filter, and such an optical filter may include an attenuator for attenuating intensity of a pulse laser beam.

Next, the diameter control unit 140 is a configuration for adjusting a diameter of a radiated laser beam or accurately focusing the laser beam onto a target point desired to be irradiated.

The diameter control unit 140 may be implemented in a convex lens for focusing a laser beam on one point and a concave lens for spreading a laser beam and may focus the lenses by selectively adjusting the distances of the convex lens and the concave lens and, at the same time, control the diameter of the radiated laser beam.

Meanwhile, the laser radiation device 100 may further include the input unit 150 and the display 160 as a configuration for assisting handling convenience of a user.

The input unit 150 is a configuration for receiving a setting input needed for driving the laser radiation device 100 from a user. The input unit 150 may be implemented in various types of input devices such as a pad, a touch screen, a mouse and the like.

On the other hand, the display 160 is a configuration for displaying an operation state and an operation result of the laser radiation device 100 or showing various kinds of information such as set parameters or the like of a laser beam to a user. The display 160 may display information input by a user or information to be provided to a user, in addition to various kinds of menus, and may be implemented as a liquid crystal display (LCD), an organic LED (OLED), a voice output device or the like.

Finally, the laser radiation device 100 further includes the control unit 170 for controlling the laser output unit 110, the frequency control unit 120, the energy control unit 130, the diameter control unit 140, the input unit 150 and the display 160 described above.

The control unit 170 may include at least one operation means and one storage means, and, at this point, the operation means may be a general-purpose central processing unit (CPU), a programmable device element implemented to be appropriate to a specific purpose (CPLD or FPGA), an application specific integrated circuit (ASIC) or a micro controller chip. In addition, a volatile memory device, a non-volatile memory device or a non-volatile electromagnetic storage device may be utilized as the storage means.

The laser radiation device 100 and the medium 200, which are components configuring the somatic sensation induction system 1000, are described above.

Hereinafter, various environments inducing a sensation of touch on a skin tissue of a user using the somatic sensation induction system 1000 according to the present invention will be described with reference to FIGS. 5 to 7.

FIG. 5 is a view showing a result of an experiment performing by radiating a laser beam on a medium 200 contacting with a skin tissue of a user, while controlling intensity and frequency of the laser beam.

The experiment of FIG. 5 generates a pulse laser beam using a neodymium; YAG laser and is progressed in a method of changing intensity and frequency of the laser beam while the pulse width and laser diameter are fixed to 8 ns and 5 nm, respectively.

It is confirmed that when the energy intensity is 8.5 mJ and in both case of radiating a laser beam to the medium 200 only once and radiating a pulse laser beam having a frequency of 5 HZ to the medium 200 for five seconds, most of the subjects recognize a feeling of touch of a certain force applied from outside. It is confirmed that, under the condition of a 20 Hz frequency, sixty percent of the subjects respond that a feeling of touch is recognized, and the other forty percent of the subjects respond that a sensation of vibration is recognized. In addition, most of the subjects recognize a sensation of vibration under the condition of a frequency of 35 Hz or higher.

On the other hand, even when the energy intensity is 14.1 mJ, 21.1 mJ or 27.4 mJ, the subjects recognize a single shot, i.e., a feeling of touch (a mechanical sensation of touch), under the condition of a 5 Hz frequency and recognize a sensation of vibration in a frequency range of 35 to 65 Hz. In addition, it is shown that some of the subjects recognize a feeling of touch and the other subjects recognize a sensation of vibration under the condition of a 20 Hz frequency.

Meanwhile, it is the same as described above that a somatic sensation which can be induced may vary according to a material used for a medium 200 contacting with a skin tissue of a user or a degree of thickness of the medium.

For example, when the condition of a radiated laser beam is a diameter of 5 mm, an energy intensity of 21.1 mJ and a frequency of 20 Hz, the user responds a feeling of i) a mechanical sensation of touch or a sensation of vibration in the case of a medium of acrylic foam (with a thickness of 2 mm) formed by layering red and white media, ii) both a mechanical sensation of touch and a sensation of heat in the case of a blue medium (with a thickness of 0.16 mm) fabricated by applying an adhesive on a man-made textile, and iii) nothing when the laser beam is radiated on an opaque medium (with a thickness of 0.08 mm) of an aluminum material.

In addition, in the case where the experiment is performed by changing the condition of the radiated laser beam to a diameter of 5 mm, an energy intensity of 21.1.mJ and a frequency of 35 Hz, the number of users feeling the sensation of heat is increased when the blue medium fabricated by applying an adhesive on a man-made textile is used, compared with a case of using a medium of acrylic foam formed of a red and white medium, and it is investigated that the users still do not feel any sensation when a medium of an aluminum material is used.

On the other hand, when a medium of an aluminum material is used, it is confirmed that a user may feel a mechanical sensation of touch and a sensation of vibration as the diameter of the radiated laser beam is smaller.

Like this, it is understood that a variety of somatic sensations can be provided to a user when the features according to a material of a medium and controllable parameters of a laser beam are combined.

Figure 6:
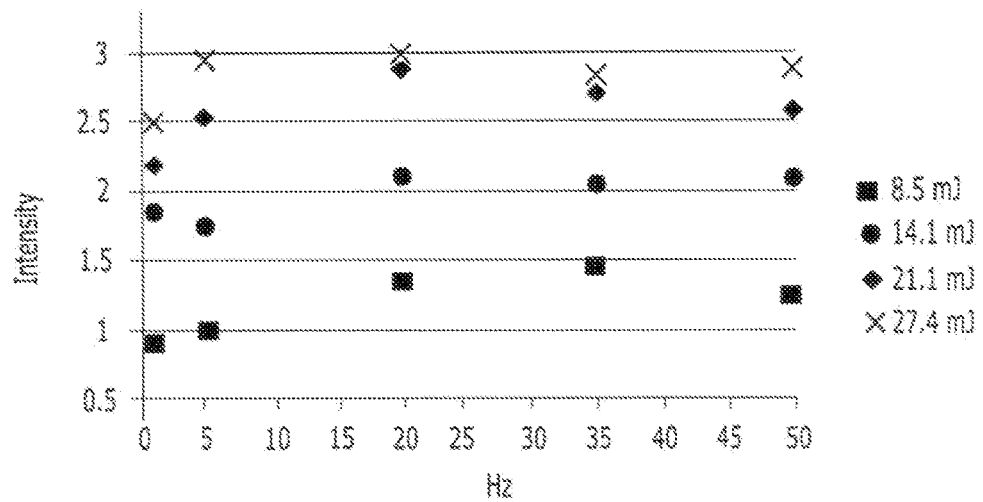
FIG. 6 is a view showing the strength of energy felt by a subject according to magnitude of energy of a laser beam.

FIG. 6 is a view showing the strength recognized by a subject according to change of intensity of a radiated laser beam. It is shown that the subjects generally recognize a further strong sensation of touch as the energy intensity increases as a result of radiating the laser beam to the medium 200 while changing intensity of the laser beam.

Figure 7:
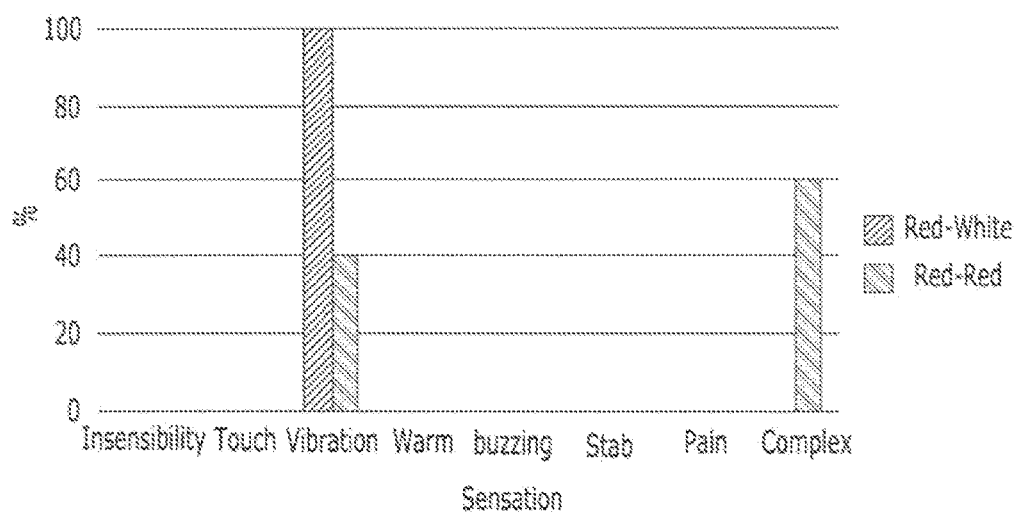
FIG. 7 is a view showing a somatic sensation felt by a subject when the absorption coefficient of a medium is changed.

FIG. 7 is a view showing a sensation of touch of a subject investigated by changing the absorption coefficient of a radiated medium 200 while intensity and frequency of a radiated laser beam are fixed.

The experiment of FIG. 7 is progressed in a method of configuring the first layer 210 and the second layer 230 of the medium 200 in red-red and red-white while the intensity, the frequency and the radiation time of the laser beam are fixed to 21.1 mJ, 70 Hz and 5 seconds, respectively.

First, when both the first layer 210 and the second layer 230 are configured in red color, it can be confirmed that forty percent of the subjects recognize a sensation of vibration and sixty percent of the subjects simultaneously recognize both a sensation of vibration and a sensation of heat under the condition of experiment described above.

On the other hand, when the first layer 210 and the second layer 230 are configured in red color and white color respectively, it is shown that the subjects recognize only a sensation of vibration.

The absorption coefficient of the medium 200 is higher in the red-red combination compared with that of the red-white combination as described in the description of the medium 200. Analyzing a result of the experiment, it can be confirmed that when a laser beam is radiated to a medium 200 of a higher absorption coefficient, a user contacting with the medium 200 recognizes a further strong sensation of touch, i.e., a sensation of heat as well as a sensation of vibration.

For reference, when a laser beam is radiated to a medium 200 of a low absorption coefficient, the subject recognizes a further strong sensation of touch as the radiation time is extended.

According to the present invention, there is an effect of inducing a somatic sensation without generating damage to a skin tissue of a user.

In addition, according to the present invention, there is an effect of providing a stimulation of a different feeling according to the absorption coefficient of a medium contacting with a skin tissue of a user.

In addition, according to the present invention, there is an effect of providing a somatic sensation of various feelings by controlling various attributes of a laser beam, e.g., energy intensity, frequency and the like of a pulse laser beam, in addition to the absorption coefficient of the medium.

In addition, according to the present invention, there is an effect of further distinctly inducing a somatic sensation compared with direct radiation of a laser beam on a skin tissue of a user.

The somatic sensation induction system 1000 according to the present invention and an environment capable of inducing various sensations of touch by the system have been described above with reference to the drawings. The embodiments of the present invention described above are disclosed for illustrative purposes, and the present invention is not limited to the embodiments. In addition, those skilled in the art may make diverse changes and modifications within the spirit and scope of the present invention, and such changes and modifications should be regarded to be included in the scope of the present invention.

What is claimed is:

1. A somatic sensation induction system comprising:
   a laser radiation device for controlling parameters of a laser beam and radiating the laser beam on one side of a medium; and
   the medium, one side of which is radiated with the laser beam, and the other side of which contacts with a skin tissue of a user,
   wherein the medium includes a first layer and a second layer which are disposed in a stacked structure between the laser radiation device and the skin tissue of the user,
   wherein each of the first layer and the second layer has a different color and absorbs a different wavelength of laser beam so that a numerical value of the absorbed wavelength and an absorbed degree of the absorbed wavelength are adjusted depending on the color of each of the first and second layers, and
   wherein each of the first layer and the second layer has an acoustic impedance smaller than an acoustic impedance of the skin tissue.

2. The system according to claim 1, wherein the parameters of the laser beam include energy intensity, pulse width, pulse frequency, stimulation time or beam diameter.

3. The system according to claim 1, wherein the first layer or the second layer is in red color or white color.

4. The system according to claim 3, wherein the wavelength of the laser beam is one of 445 nm, 480 nm, 532 nm, 650 nm, 809 nm, 850 nm and 1064 nm.

5. The system according to claim 4, wherein the first layer and the second layer are respectively in red color and white color, and a sensation of touch is induced on the skin tissue of the user by controlling a pulse frequency of the laser beam between 1 Hz and 25 Hz.

6. The system according to claim 4, wherein the first layer and the second layer are respectively in red color and white color, and a sensation of vibration is induced on the skin tissue of the user by controlling a pulse frequency of the laser beam to be 25 Hz or higher.

* * * * *